(12) United States Patent
Frewin et al.

(10) Patent No.: US 10,136,825 B2
(45) Date of Patent: Nov. 27, 2018

(54) LONG-TERM IMPLANTABLE SILICON CARBIDE NEURAL INTERFACE DEVICE USING THE ELECTRICAL FIELD EFFECT

(71) Applicants: Christopher Leroy Frewin, Tampa, FL (US); Stephen E. Saddow, Odessa, FL (US)

(72) Inventors: Christopher Leroy Frewin, Tampa, FL (US); Stephen E. Saddow, Odessa, FL (US)

(73) Assignee: University of South Florida, Tampa, FL (US)

(*) Notice: Subject to any disclaimer, the term of this patent is extended or adjusted under 35 U.S.C. 154(b) by 1242 days.

(21) Appl. No.: 14/154,863

(22) Filed: Jan. 14, 2014

(65) Prior Publication Data
US 2014/0194719 A1  Jul. 10, 2014

Related U.S. Application Data (63) Continuation of application No. PCT/US2012/046884, filed on Jul. 16, 2012.
(Continued)

(51) Int. Cl.
*A61B 5/04* (2006.01)
*A61B 5/0478* (2006.01)
(Continued)

(52) U.S. Cl.
CPC ........ *A61B 5/04001* (2013.01); *A61B 5/0478* (2013.01); *H01L 21/28* (2013.01); *H01L 29/66477* (2013.01); *A61B 2562/125* (2013.01)

(58) Field of Classification Search
CPC ... H01L 29/51; H01L 29/2003; A61B 5/0478; A61B 5/04001
See application file for complete search history.

(56) References Cited

U.S. PATENT DOCUMENTS 6,686,131 B2   2/2004 Elian
2003/0205754 A1* 11/2003 Forbes .............. H01L 21/28273
                                                 257/314
(Continued)

FOREIGN PATENT DOCUMENTS

WO   2011066552 A2   6/2011

OTHER PUBLICATIONS

Extended Search Report issued by the European Patent Office dated Mar. 24, 2015 for European Patent Application No. 12810659.8-1657.
(Continued)

*Primary Examiner* — Michael D Abreu
(74) *Attorney, Agent, or Firm* — Molly L. Sauter; Smith & Hopen, P. A.

(57) ABSTRACT

Field effect devices, such as capacitors and field effect transistors, are used to interact with neurons. Cubic silicon carbide is biocompatible with the neuronal environment and has the chemical and physical resilience required to withstand the body environment and does not produce toxic byproducts. It is used as a basis for generating a biocompatible semiconductor field effect device that interacts with the brain for long periods of time. The device signals capacitively and receives signals using field effect transistors. These signals can be used to drive very complicated systems such as multiple degree of freedom limb prosthetics, sensory replacements, and may additionally assist in therapies for diseases like Parkinson's disease.

14 Claims, 4 Drawing Sheets

Related U.S. Application Data (60) Provisional application No. 61/507,687, filed on Jul. 14, 2011.

(51) Int. Cl.
*H01L 21/28* (2006.01)
*H01L 29/66* (2006.01)

(56) References Cited

U.S. PATENT DOCUMENTS

| | | |
|---|---|---|
| 2008/0195220 A1 | 8/2008 | Pope et al. |
| 2008/0242071 A1* | 10/2008 | Wang ............... H01L 21/28185 438/591 |
| 2009/0149918 A1 | 6/2009 | Krulevitch et al. |
| 2010/0075438 A1 | 3/2010 | Ho et al. |
| 2010/0106233 A1 | 4/2010 | Grant et al. |
| 2010/0255447 A1 | 10/2010 | Biris et al. |
| 2010/0303706 A1 | 12/2010 | Wallace et al. |

OTHER PUBLICATIONS

C.L. Frewin et al. "The neuron-silicon carbide interface: Biocompatiblity study and BMI device development", Graduate School Theses and Dissertations, May 28, 2009, XP055140751, pp. 154-156.

Vassanelli and Fromherz. Transistor records of excitable neurons from rat brain. Applied Physics A. 1998. vol. 66: 459-463.

Stett et al., Two-way silicon-neuron interface by electrical induction. Physical Review E. 1997. vol. 55 (No. 2): 1779-1782.

Fromherz and Stett. Silicon-Neuron Junction: Capacitive Stimulation of an Individual Neuron on a Silicon Chip. Physical Review Letters. 1995. vol. 75 (No. 8): 1670-1674.

Fromherz et al., Neuron Transistor: Electrical Transfer Function Meadsured by the Patch-Clamp Technique. Physical Review Letters. 1993. vol. 71 (No. 24): 4079-4083.

Fromherz. Neuroelectronic Interfacing: Semiconductor Chips with Ion Channels, Nerve Cells, and Brain. Nanoelectronics and Information Technology. Rainer Waser, Wiley-VCH. Berlin. 2003: 781-810.

Fromherz. Neuron-Silicon Junction of Brain-Computer Junction? Ars Eletronica Festival. Eds. G. Stocker, C. Schopf. Springer. Wien. 1997: 158-161.

Carlisle. Silicon as an essential trace element in animal nutrition. Ciba Foundation Symposium 121. Wiley. Chichester. 1986: 123-139.

Braun and Fromherz. Fast Voltage Transients in Capacitive Silicon-to-Cell Stimulation Detected with a Luminescent Molecular Electronic Probe. Physical Review Letters. 2001. vol. 86 (No. 13): 2905-2908.

Besl and Fromherz. Transistor array with an organotypic brain slice: field potential records and synaptic currents. European Journal of Neuroscience. 2002. vol. 15: 999-1005.

Ohshima et al., The electrical Characteristics of Metal-Oxide-Semiconductor Field Effect Transistors Fabricated on Cubic Silicon Carbide. Jpn. J. Appl. Phys. 2003. vol. 42. Part 2 (No. 6B): L625-L627.

International Search Report and Written Authority for PCT/US2012/046884 (Filing Date: Jul. 16, 2012) dated Jan. 10, 2013; Applicant: University of South Florida et al.

Preliminary Report of Patentability for PCT/US2012/046884 (filing date Jul. 16, 2012) dated Jan. 23, 2014; Applicant: University of South Florida et al.

* cited by examiner

LONG-TERM IMPLANTABLE SILICON CARBIDE NEURAL INTERFACE DEVICE USING THE ELECTRICAL FIELD EFFECT

CROSS-REFERENCE TO RELATED APPLICATIONS

This non-provisional application is a continuation of currently pending PCT Application No. PCT/US2012/046884 filed Jul. 16, 2012, which claims priority to U.S. Provisional Patent Application No. 61/507,687, filed on Jul. 14, 2011 and entitled, "Long Term Implantable Silicon Carbide Neural Interface Device using the Electrical Field Effect" by the same inventors; the contents of which are hereby incorporated by reference.

BACKGROUND OF THE INVENTION

This invention relates, generally, to neuronal interface devices. More particularly, it relates to such a device that replaces silicon with cubic silicon carbide.

Silicon is known to be used in the manufacturing of bipolar junction transistors, junction field effect transistors, and metal insulator transistor devices.

Field effect devices constructed from silicon and silicon dioxide have been used to interact with neurons by receiving and sending signals. Field effect devices, unlike electrode based devices, use a high electrical impedance to influence the electrochemical environment within the body. Unfortunately, field effect devices are ineffective for use over long periods of time for several reasons. One known disadvantage to field effective devices is that sodium ions may diffuse through the oxide and create a fixed positive charge at the interface, which an undesirable result. More importantly, silicon and silicon oxide have been proven to be non-biocompatible for use as an implantable neural device.

The majority of semiconductors which could replace silicon are also known to be toxic. However neural devices must, by necessity, be implanted permanently so they must be very robust and, to date, a semiconductor-based neural device, such as a brain-machine interface (BMI), has failed to perform adequately for long-term chronic implantations.

The field of implantable brain machine interfaces (BMIs), also known as brain computer interfaces (BCIs), is a burgeoning technology developed by engineers, neurologists, and computer scientists that has the potential to offer hope and possible cures for many problems associated with the central nervous system.

A BMI and BCI device allows reception of electrical pulses generated by neurons and transfer of the electrical pulses to external devices where they may be used as control signals for the nervous system. BMI devices known in the art utilize penetrating, invasive interfaces directly accessing the signals from nearby neurons. The proximity of the BMI device to these neurons also allows the direct stimulation of these signals, known as action potentials, and can thereby create true closed loop control systems.

Implantable devices, such as BMIs, inherently possess a larger content and quality of information, and therefore can easily outperform other interface techniques such as electroencephalography (EEG) and electrocortiography (ECG). Although implantable devices allow for closed loop control and sensory feedback, and the information they acquire can control complicated BMI systems, these systems still experience major difficulties which are blocking their widespread usage.

Conventional implantable neural interface devices use four well-established architectures: 1) Macroelectrode wire implants; 2) Microelectrode wire arrays; 3) The Utah intracortical electrode array (UIEA); and 4) The Michigan planar microelectrode. These devices operate through conductive electrical transducers (i.e., electrodes) which interface and react with the electrolytic fluid surrounding the cells in the body. The ionic and electron changes, movement within and surrounding electrodes and electrical activity of the cells allow signal transport in both directions. This interaction can either be a capacitive interaction through the formation of a Helmholtz double layer, or it can be Faradaic which involves oxidation or reduction chemistry at the electrode surface. Capacitive charge transfer does not generate any chemical reaction, but can be limited by geometrical surface area. On the other hand, Faradaic reactions at the electrode surface can provide high levels of charge transfer, but the high transfer rates can lead to irreversible processes which damage both the electrode and surrounding cells.

Electrodes, both in vitro and in vivo, have displayed many problems that can lead to the reduced reliability which has been observed with implantable neural devices. Faradaic reactions can electrolyze water, produce pH changes, and produce gasses and reactive ionic species. Another consideration is that electrode polarization is over two (2) times greater in vivo, which is thought to be the result of protein and molecule absorption onto the electrode surface as well as an increased ionic resistance within tissue surrounding the implant. The surface absorption of various molecules can lead to an increase in the impedance of the electrode, which reduces the signal to noise ratio and decreases the high frequency response.

The geometrical surface area of the electrode also has a large effect on the ability of an electrode to withstand charge transfer changes, and larger electrodes are generally better able to withstand the charge densities required to stimulate neural responses without deterioration. It has been deduced that maintaining a charge balance during stimulation by using biphasic wave forms helps reduce damage to the electrode and surrounding tissue.

An alternative to electrode interaction with neurons was developed by P. Fromherz from the Max-Planck-Institute. In 1985 he presented the idea that silicon (Si) devices and brains could be directly coupled without electrode transducers. He has since shown that Si metal-oxide-semiconductor capacitors (MOScaps) can stimulate neuronal membrane depolarization, and Si metal-oxide-semiconductor field effect transistors (MOSFET) can receive electrical signals from neurons. The major advantage of MOS, and the related device, metal-insulator-semiconductor (MIS), is that they interact with the cell using capacitive/electric field effects. The MIS devices avoid the material and tissue damaging Faradaic reactions which are encountered with electrode transducers. As a further bonus, the device operation is based around electric fields generated on the opposite sides of an insulating material and, due to this action, they are not as susceptible to increases in tissue impedance, as they are constructed with highly insulating, high impedance, capacitive functionality.

Another advantage of FET devices is that they can be interlinked into arrays by combining common connections, thereby reducing the amount of feed-through wiring required and allowing many more active interaction areas on the neural interface, with current art showing 16,384 contacts per square millimeter. Finally, unlike electrode transducer devices, stimulation of neuronal action potentials with FET capacitor devices maintains the charge balance through a single monophasic pulse which dissipates naturally through RC parasitic losses when the signal is removed.

Initially, Fromherz et al. used MOSFET transistors with no gate metal to receive action potential signals from an electrically active neuron. This interaction occurs because the ionic metals in the extracellular solution form the gate metal charge at the oxide interface. This interaction creates a series capacitive coupling between the gate oxide and the cell membrane. The two (2) capacitors have a parallel parasitic resistance which Fromherz et al. labels the transductive extracellular potential, but it has also been referred to as the sealing resistance by others who were investigating the electrical model for electrode transducers.

Unlike the passive operation of an electrode, signals are intercepted by the MOSFET through a different method. The MOSFET is driven into saturation, or active mode, ($V_{sd}>|V_{gs}-V_{th}|$, $V_s=V_b=VDD$, and $VDD>>V_{sd}$) which provides a constant current flow through the device. In saturation, the MOSFET drain current is directly controlled by fluctuations in the gate voltage. The extracellular ionic flux generated by a neuronal action potential changes ionic and displacement currents within the transductive extracellular potential, which changes the charge on the gate oxide, and then is transferred to the depletion region within the gate and modulates the drain current within the MOSFET device.

Stimulation of an action potential in a neuron can also be achieved through a similar field effect device, the metal-oxide-semiconductor capacitor, or MOScap. Fromherz et al. show that this device uses the same principles that allow the transistor device to function. A buried conductive channel under an oxide on a MOScap is stimulated with a voltage which gives rise to ionic and displacement currents on the opposite side of the insulator. The fields generated at the oxide surface modulate the transductive extracellular voltage to depolarize the membrane, and if this voltage was greater than the threshold voltage of the neuron, a neuronal action potential is produced. The combination of the MOScap and MOSFET devices allow bi-directional signaling, and can be used with digital electronic processing to create bridges between different neuronal cells.

Fromherz et al. have developed this technology in Si to the point where they can interface with complex neural tissue, single neuronal cells, voltage controlled ionic gates in the cellular membrane, and even the chemicals that pass between active synapses. These capabilities place this device far ahead of the electrode devices, but there are many problems that this type of device must overcome if it will have resiliency in vivo.

Reliability of implanted field effect devices within the body environment is one of the major issues that prevents this technology from being used outside neurology and electrophysiology laboratories. One of the greatest problems with Si-based field effect devices is their susceptibility to contamination from metallic ions, such as sodium (Na), potassium (K), and iron (Fe). This problem is well known in the semiconductor industry, and is one of the driving forces behind the development of the cleanroom for processing electronic devices. Metallic ions diffuse through the insulating silicon dioxide ($SiO_2$) layer and create fixed positive charges at the interface, which degrades the reliability and functionality of field effect devices. These devices are in direct contact and interacting with the extracellular fluid, or cerebral spinal fluid, which contains copious amounts of $Na^+$, $K^+$, $Cl^-$, $Ca^{+2}$, and $Mg^{+2}$ ions.

Another important consideration is that both Si and $SiO_2$ are not necessarily biocompatible, and may provide negative biological effects, like cancer and Alzheimer's disease, when used for applications in implantable brain machine interfaces. Many modern semiconductors which could be substituted for Si possess many of the same problems with respect to immunoreactivity, or these materials produce toxic byproducts due to their atomic constituents (i.e. gallium, arsenic, indium, antimony, etc.).

However, in view of the art considered as a whole at the time the present invention was made, it was not obvious to those of ordinary skill in the art how the art of neuronal interface devices could be advanced.

SUMMARY OF THE INVENTION

The long-standing but heretofore unfulfilled need for an improved neuronal interface device is now met by a new, useful, and non-obvious invention.

The novel structure includes a biocompatible, chemically inert semiconductor that replaces silicon in neuronal interface devices. The novel neuronal interface device includes a base material formed of cubic silicon carbide and an insulator formed of biocompatible and chemically resistant materials such as amorphous silicon carbide or diamond.

In a particular embodiment, an implantable neural interface device in accordance with the present invention may include, a control unit and at least one substantially planar neural probe coupled to the hermetically sealed control unit, each of the at least one neural probes comprising. The neural probe may further include, at least one electrolyte insulator semiconductor capacitor (EISCap) having a cubic silicon carbide (3C—SiC) base and a biocompatible and chemically resistant gate insulator and at least one field effect transistor having a cubic silicon carbide (3C—SiC) base.

In operation, the novel neural interface may be implanted within a neural environment to communicate with neural tissue in situ by operating the electrolyte insulator semiconductor capacitor to generate an electric field to stimulate the neural tissue and operating the field effect transistor to receive the electric field generated by the neural tissue as a result of the stimulation.

An important object of the invention is to overcome the limitations of prior art field effect devices constructed from silicon and silicon dioxide.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

This present invention provides for a long term biocompatible neural implant utilizing field effect devices. Each component of the invention may be formed of many related materials.

Figure 1:
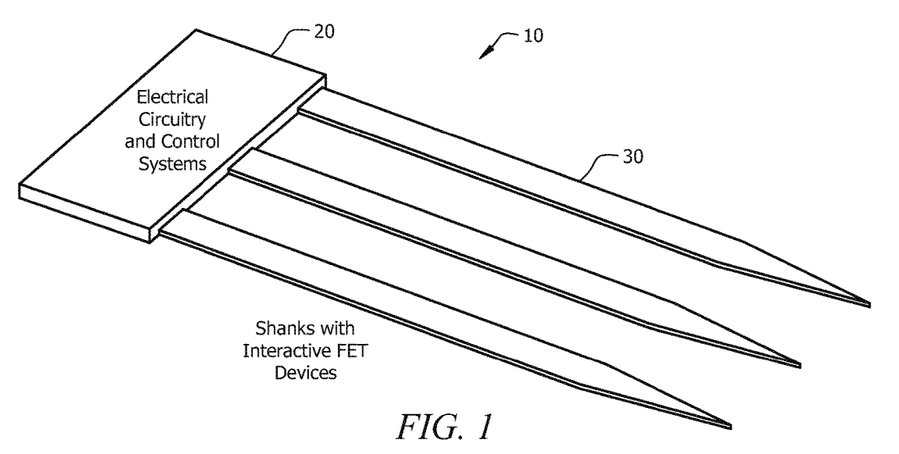
FIG. 1 is a perspective view of the novel structure in accordance with an embodiment of the present invention.

FIG. 1 depicts an illustrative embodiment of the novel of the present invention, which is denoted as a whole by the reference numeral 10. The novel structure includes two (2) primary sections, as depicted in FIG. 1. The first section, labeled 20 in FIG. 1, contains the control and routing circuitry for the signals, the signal generation circuit, the signal processing circuit (amplifiers, filters, and analog to digital converters), the wireless communication system, and the power receiving or supply system. The power system may contain either a wireless power reception system or a rechargeable battery supply.

The second section 30 in FIG. 1 is implanted into the tissue and interacts directly within the neural environment. Although the depicted device includes three (3) planar "Michigan Probe" style probes, there is no limit to how many multiple planar probes can be constructed in parallel. Nor is there a limit to the number of the 'comb' like parallel devices which can be set into arrays to create a three dimensional device. This system is composed of a sharpened protrusion, which is attached to the first section 20 through wafer bonding techniques or connected using flexible wires coated with chemically resistant polymers. As the polymers will not penetrate the neural environment, they last longer than expected. The surface of the planar probe, which interacts with the neuronal environment, contains an assortment of up to three (3) types of FET devices. Cubic silicon carbide (3C—SiC) is the base physical material for the generation of the FET devices. Graphene can be produced directly on 3C—SiC, and diamond is a cubic structure and can also be grown on 3C—SiC. All reference hereinafter to 3C—SiC should be understood to include diamond and graphene as well since said materials may replace 3C—SiC.

The insulating materials and conducting materials are interchangeable as mentioned previously.

More particularly, the field effect devices in this invention may be formed of three (3) different semiconductor materials: 3C—SiC, diamond, and graphene. Although 3C—SiC and diamond are materials known to have utility in the construction of field effect devices, graphene has utility as a transistor element as well. Each of these materials is physically and chemically robust, and has appreciable levels of biocompatibility. The devices within this invention include amorphous SiC (a-SiC), polycrystalline SiC (poly-SiC), and insulating diamond as insulator material to generate the gate fir the field effect devices. Diamond can be in single-, poly-, nano-, or ultracrystalline form. The same materials can be used for the isolation material, but nominally the material with the best deposition rate and insulating properties are used. Metal conductors are replaced with carbon conductors. The conductors are graphene and graphitized carbon from pyrolyzed polymers (i.e. photoresist). Specifically, a semiconductor based active device generates and receives electric fields for the communication with neurons, thereby replacing the non-biocompatible Si-based neural prosthetic devices.

Due to the complexity of the circuitry required for the control circuitry 20 of the device 10, silicon is used as a base semiconductor material due to the level of processing technology necessary to complete complex circuits as well as the large array of processing techniques available. The Si derivative $SiO_2$ is used for quality insulation (i.e. gate insulation) and $Si_3N_4$ is used for a device isolation material. Metals like Au, Pt, chrome, polysilicon, etc., have utility as the device conductors and interconnect "feed-thrus" to the devices on the implantable field effect devices 30.

Si and its derivatives have biocompatibility and chemical resistivity issues, so the control circuitry 20 must be hermetically sealed to both protect its functionality, as well as protect the body from the possible deterioration of the device. Hermetic sealing in amorphous SiC (a-SiC) or nanocrystalline/ultracrystalline diamond are good hermetic sealing agents as they have physical and chemical robustness and they have been used in long term implants before.

Figure 2A:
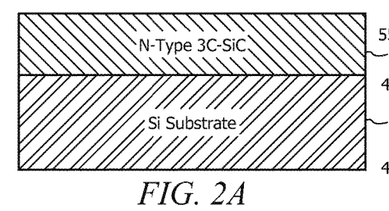
FIG. 2A depicts the first general processing stage for the primary neuronal action potential activation device, i.e., the electrolyte insulator semiconductor capacitor, in accordance with an embodiment of the present invention.

The primary neuronal action potential activation device is the 3C—SiC EIScap, or electrolyte insulator semiconductor capacitor. The general processing stages for this device are shown with reference to FIG. 2. In an exemplary embodiment, at stage 2A, the process consists of growing a homoepitaxial film 40 onto the surface of a cubic substrate 45. Si is the cheapest method of the heteroepitaxial growth for 3C—SiC, and it also provides additional processing benefits through its chemical susceptibility. Single crystal diamond and hexagonal forms of SiC (4H— and 6H—SiC) can also be used as substrates for 3C—SiC growth, but are considerably harder to remove.

Figures 2B, 2C, 2D, 2F, 2G, 2H, 2I:
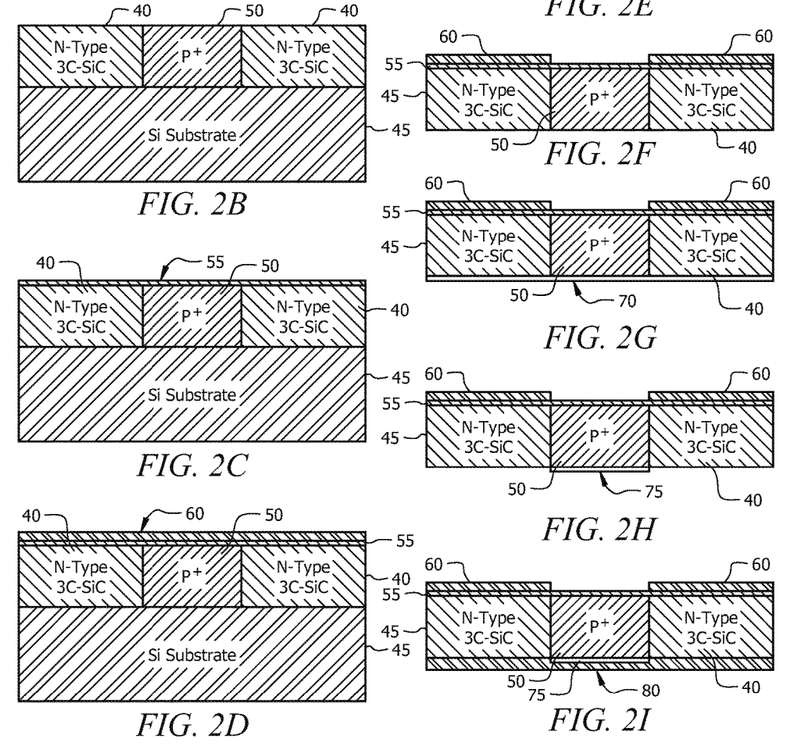
FIG. 2B depicts the second general processing stage for the primary neuronal action potential activation device, i.e., the electrolyte insulator semiconductor capacitor, in accordance with an embodiment of the present invention.
FIG. 2C depicts the third general processing stage for the primary neuronal action potential activation device, i.e., the electrolyte insulator semiconductor capacitor, in accordance with an embodiment of the present invention.
FIG. 2D depicts the fourth general processing stage for the primary neuronal action potential activation device, i.e., the electrolyte insulator semiconductor capacitor, in accordance with an embodiment of the present invention.
FIG. 2F depicts the sixth general processing stage for the primary neuronal action potential activation device, i.e., the electrolyte insulator semiconductor capacitor, in accordance with an embodiment of the present invention.
FIG. 2G depicts the seventh general processing stage for the primary neuronal action potential activation device, i.e., the electrolyte insulator semiconductor capacitor, in accordance with an embodiment of the present invention.
FIG. 2H depicts the eighth general processing stage for the primary neuronal action potential activation device, i.e., the electrolyte insulator semiconductor capacitor, in accordance with an embodiment of the present invention.
FIG. 2I depicts the ninth general processing stage for the primary neuronal action potential activation device, i.e., the electrolyte insulator semiconductor capacitor, in accordance with an embodiment of the present invention.

N-type 3C—SiC 40 may be grown on Si 45 through the introduction of nitrogen gas during intrinsic epitaxial growth during the first stage of processing. For stage 2B, photolithographic methodology is employed to generate a protective mask 50 on the 3C—SiC 20. Neurons require a high level of charge transfer, and the doping is increased by the ion implantation of aluminum ions ($Al^{+3}$). 3C—SiC domains grow at different rates, so the surface has a mesa like appearance.

To ensure that there are no charge irregularities due to surface geometry, the 3C—SiC wafer is CMP (chemically mechanically polished) polished flat, chemically cleaned, and etched in a high temperature hydrogen ambient to reveal an atomically flat surface.

For stage 2C, a thin layer of high quality insulation material 50 is grown or deposited to generate the gate of the device. The deposition method depends on the materials selected.

Stage 2D requires the deposition of the device isolation material 60, which may be of lower quality than the gate insulator due to the trade-off in deposition speed and thickness.

Figure 2E:
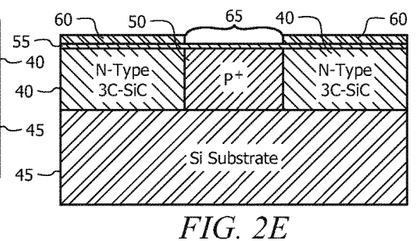
FIG. 2E depicts the fifth general processing stage for the primary neuronal action potential activation device, i.e., the electrolyte insulator semiconductor capacitor, in accordance with an embodiment of the present invention.

Stage 2E uses lithography to generate the protective mask, and a window 65 is etched in the isolation material 60 down to the gate insulation 50. Unlike Si, there are no convenient chemical etching processes for SiC, so DRIE or RIE are regularly employed instead.

At Stage 2F the Si substrate wafer 45 is removed to create a free-standing device. This removal can be achieved using one of many methods of dry or wet chemical etching. At the end of stage 2F, the released 3C—SiC film is cleaned, and the 3C—SiC interface defects are etched away by DRIE/RIE etching. Etching a few microns into the 3C—SiC material removes many of the defects generated during heteroepitaxial crystal growth.

After careful CMP planarization, polishing, and $H_2$ etching, stage 2G is used to deposit/grow a thin film of one of the novel conductors 70 onto the backside of the 3C—SiC wafer.

The conductor network 75 is generated in stage 2H through lithography and etching. An alternative for the masking followed by the etching performed in stages 20 and 2H is the lift-off process. In the lift-off process, starting in stage 20, but perform the lithography first, and the conductor 70 is deposited on top of the lithographic mask and the exposed surfaces. In stage 2H, the polymer mask is dissolved away, taking the excess conductor with it and revealing the completed conductor network 75 for the device. This alternative lift-off process is temperature dependent as most polymers cannot withstand the temperatures required to epitaxially generate graphene on the face of 3C—SiC, but it is an alternative nonetheless.

The last stage, stage 2I, requires cleaning the wafer and coating the conductor network 75 with a thick film of insulation material 80. This is followed by high temperature annealing in an ambient gas such as argon, Ar. This activates the doping ions within the 3C—SiC crystal lattice, as well as repairs some of the crystal damage from the ion implantation.

The EIScap sends signals to neural tissue (i.e., perform stimulation), but a field effect transistor (FET)) is needed to intercept the ionic changes which are generated during a neuronal action potential in order to have a complete neural implantation device (i.e., signal recording).

The FET device used to intercept the ionic changes at the neural interface may be a junction field effect transistor (JFET). This is a simple transistor and does not require a gate insulator. The general processing stages for the JFET are illustrated with reference to FIG. 3.

Figure 3A:
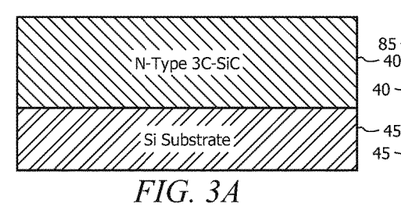
FIG. 3A depicts the first general processing stage for making a field effect transistor for intercepting the ionic changes which are generated during a neuronal action potential in order to have a complete neural implantation device, in accordance with an embodiment of the present invention.

Stage 3A begins with the same processing stages used for the EIScap, as both of these devices are required to be eventually generated side by side and at the same time on the same interface.

Figure 3B:
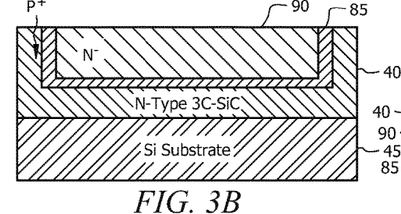
FIG. 3B depicts the second general processing stage for making a field effect transistor for intercepting the ionic changes which are generated during a neuronal action potential in order to have a complete neural implantation device, in accordance with an embodiment of the present invention.

Stage 3B involves using photolithography to generate a mask for deep ion implantation of aluminum ions ($Al^{+3}$) which will lay the foundation for the p-stop isolation 85 for the JFET. A second ion implantation of nitrogen ions ($N^{-3}$) generates the location of the n-channel 90 for the JFET.

Figure 3C:
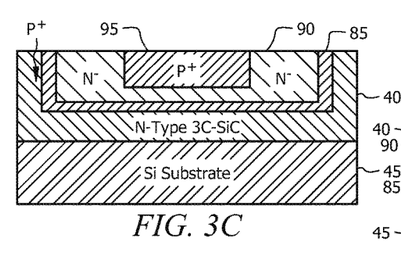
FIG. 3C depicts the third general processing stage for making a field effect transistor for intercepting the ionic changes which are generated during a neuronal action potential in order to have a complete neural implantation device, in accordance with an embodiment of the present invention.

The surface is cleaned to remove the masks, and a final mask is generated for the implanting of the p-type gate junction 95 during stage 3C. The extra ion implantation is preferred because a p-channel 3C—SiC JFET would not be as efficient as the n-channel due to a much lower hole mobility than electron mobility.

Figure 3D:
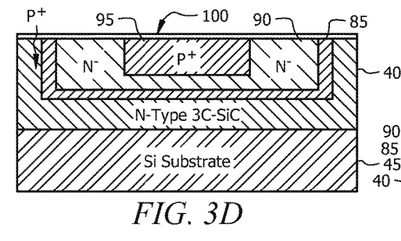
FIG. 3D depicts the fourth general processing stage for making a field effect transistor for intercepting the ionic changes which are generated during a neuronal action potential in order to have a complete neural implantation device, in accordance with an embodiment of the present invention.

Stage 3D consists of the generation of a thin film layer of the preselected conductor material 100, which is followed by a lithographic generated mask.

Figure 3E:
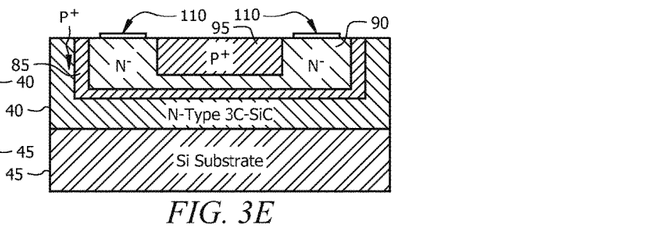
FIG. 3E depicts the fifth general processing stage for making a field effect transistor for intercepting the ionic changes which are generated during a neuronal action potential in order to have a complete neural implantation device, in accordance with an embodiment of the present invention.

The conductor network 110 is revealed through etching in stage 3E. As with the production of the EIScap, stages 3D and 3E could be accomplished using the lift-off method as an alternative to blanket film etching. The area above the junction 95 is conductor free, and the electrolyte metals ($Na^+$, $K^+$, $Ca^{+2}$, $Mg^{+2}$, $Cl^-$) are used to modulate the width of the depletion layer within the n-channel.

Figure 3F:
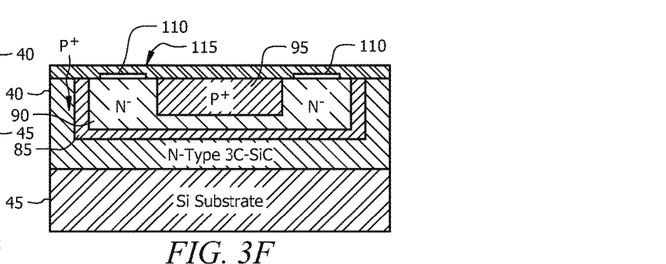
FIG. 3F depicts the sixth general processing stage for making a field effect transistor for intercepting the ionic changes which are generated during a neuronal action potential in order to have a complete neural implantation device, in accordance with an embodiment of the present invention.

Stage 3F coats the entire surface of the wafer with the electrical isolation material 115.

Figure 3G:
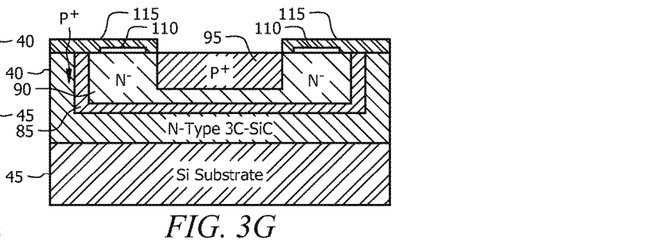
FIG. 3G depicts the seventh general processing stage for making a field effect transistor for intercepting the ionic changes which are generated during a neuronal action potential in order to have a complete neural implantation device, in accordance with an embodiment of the present invention.

Stage 3G uses photolithography to open the gate windows 95 through the insulation material 115.

Figure 3H:
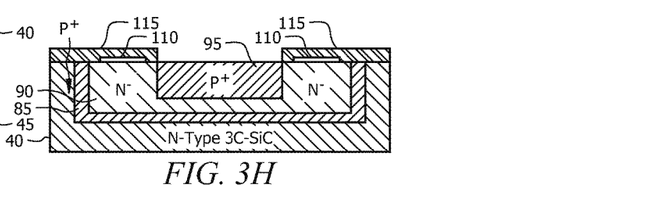
FIG. 3H depicts the eighth general processing stage for making a field effect transistor for intercepting the ionic changes which are generated during a neuronal action potential in order to have a complete neural implantation device, in accordance with an embodiment of the present invention.

Stage 3H finishes the device by removing the Si substrate 45, and annealing the SiC 40 to allow activation of the dopant ions into the crystal lattice.

Figure 4A:
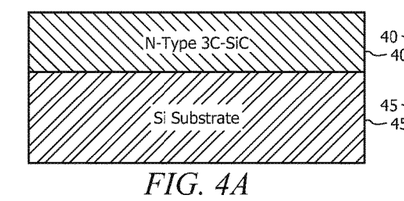
FIG. 4A depicts the first general processing stage for making the second transistor, i.e., a 3C—SiC EISFET, in accordance with an embodiment of the present invention.
Figures 4B, 4C, 4D, 4F, 4G, 4H:
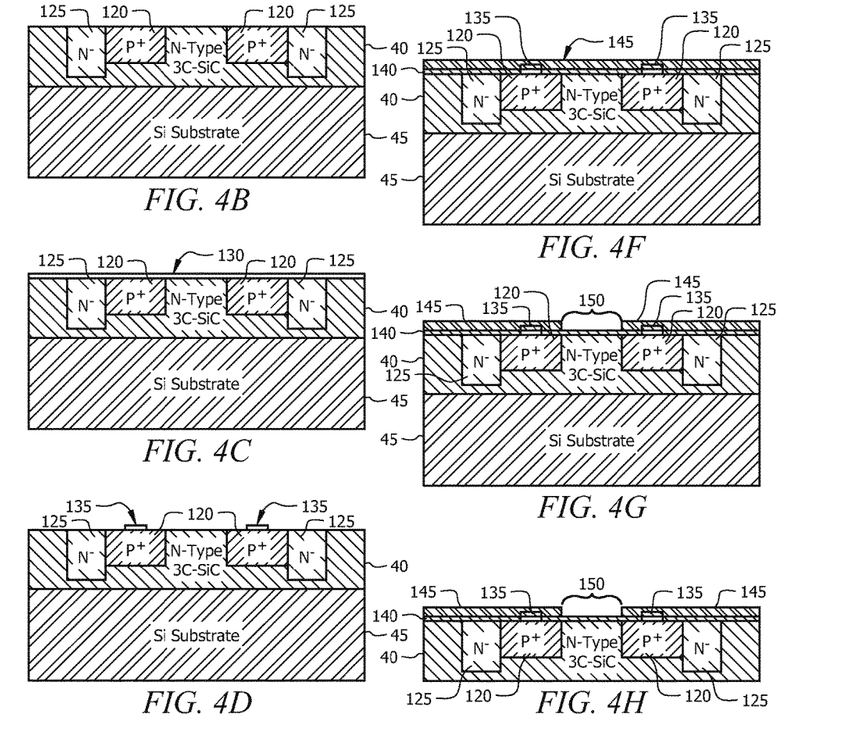
FIG. 4B depicts the second general processing stage for making the second transistor, i.e., a 3C—SiC EISFET, in accordance with an embodiment of the present invention.
FIG. 4C depicts the third general processing stage for making the second transistor, i.e., a 3C—SiC EISFET, in accordance with an embodiment of the present invention.
FIG. 4D depicts the fourth general processing stage for making the second transistor, i.e., a 3C—SiC EISFET, in accordance with an embodiment of the present invention.
FIG. 4F depicts the sixth general processing stage for making the second transistor, i.e., a 3C—SiC EISFET, in accordance with an embodiment of the present invention.
FIG. 4G depicts the seventh general processing stage for making the second transistor, i.e., a 3C—SiC EISFET, in accordance with an embodiment of the present invention.
FIG. 4H depicts the eighth general processing stage for making the second transistor, i.e., a 3C—SiC EISFET, in accordance with an embodiment of the present invention.
Figure 4E:
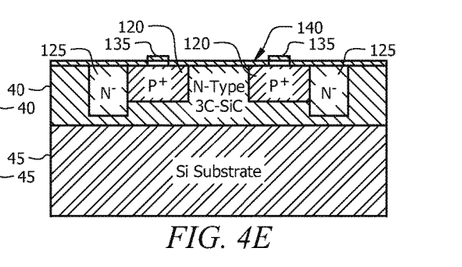
FIG. 4E depicts the fifth general processing stage for making the second transistor, i.e., a 3C—SiC EISFET, in accordance with an embodiment of the present invention.

The second transistor may be a 3C—SiC EISFET, as depicted with reference to FIG. 4.

Stage 4A is the same as the previous two devices with growth of n-type 3C—SiC 40 on a Si substrate 45.

At stage 4B, lithography is used to generate two masks. The first is for the ion implantation of the p-type source and drain wells 120, and a second mask provides the template for the $n^-$ isolation wells 125.

At stage 4C, the conductor 130 selected for the device manufacture is grown on, or deposited on, the surface of the 3C—SiC, and lithography and etching are used to generate the conductive pathways 135 for the source and drain in stage 4D. Stages 4C and 4D can be interchanged with the liftoff method as previously described.

In stage 4E, the development of the conductive pathways 135 is followed by the deposition of a high quality insulator material 140, used for the gate material.

The 4E stage is followed by the deposition of the isolation material 145 in stage 4F.

Stage 4G begins with lithographic generation of the mask, and subsequent etching of the window 150 for the buried gate material 40.

Finally, in stage 4H, the Si substrate 45 is removed and the device is annealed to activate the dopant material.

The devices described above are combined in pairs on the surface of the shank. They are distributed according to the target area within the brain to efficiently interact with the neurons/neural bundles. Bi-directional signaling is simply made by combining an EIScap device signal with either a JFET or EISFET device running in saturated mode. Much of the required wiring for the manipulation of the three terminal FET systems can be consolidated by generating a switching grid system within the first section of the device 20, and multiple emitters, or conductors, can be interlaced in the same way. Finally, to generate active layers on both sides of the planar device, a second round of processing is used on the opposite face of the 3C—SiC shank after removal of the silicon base.

The realization of two-sided devices could also be realized with wafer binding techniques, but the bonding material must possess biocompatibility at least as acceptable as the materials disclosed herein.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An implantable neural interface device, the device comprising:
   a control unit;
   at least one substantially planar neural probe coupled to the control unit, each of the at least one substantially planar neural probes comprising;
      at least one neural tissue stimulation device comprising at least one electrolyte insulator semiconductor capacitor (EISCap) having a cubic silicon carbide (3C—SiC) base and a biocompatible and chemically resistant gate insulator, wherein neural tissue in contact with the electrolyte insulator semiconductor capacitor (EISCap) forms a gate conductor to generate an electric field to stimulate the neural tissue at least partially surrounding the at least one substantially planar neural probe; and
      at least one neural tissue stimulation receiving device comprising at least one field effect transistor having a cubic silicon carbide (3C—SiC) base, wherein neural tissue in contact with the at least one field effect transistor forms a gate conductor and wherein the at least one neural tissue stimulation receiving device receives ionic changes generated by the neural tissue resulting from the electric field stimulation by the at least one neural tissue stimulation device.

2. The device of claim 1, wherein the control unit is hermetically sealed.

3. The device of claim 2, wherein the conductive network is formed of graphene or pyrolized polymers.

4. The device of claim 1, wherein the control unit comprises circuitry selected from the group consisting of control circuitry, routing circuitry, signal generation circuitry, signal processing circuitry, wireless communication system circuitry and power system circuitry.

5. The device of claim 4, wherein the power system circuitry comprises a power supply selected from the group consisting of a rechargeable battery supply and a wireless power reception supply.

6. The device of claim 4, wherein the conductive network is formed of graphene or pyrolized polymers.

7. The device of claim 1, wherein the gate insulator is silicon carbide.

8. The device of claim 7, wherein the silicon carbide is selected from the group consisting of amorphous silicon carbide and polycrystalline amorphous silicon carbide.

9. The device of claim 1, wherein the electrolyte insulator semiconductor capacitor further comprises a conductive network.

10. The device of claim 1, wherein the field effect transistor further comprises a conductive network.

11. The device of claim 1, wherein the field effect transistor is a junction field effect transistor (JFET) and wherein the JFET does not include a gate insulator.

12. The device of claim 1, wherein the field effect transistor is an electrolyte insulator semiconductor field effect transistor (EISFET).

13. The device of claim 1, wherein the gate insulator is diamond.

14. The device of claim 13, wherein the diamond is selected from the group consisting of single crystalline diamond, polycrystalline diamond, nanocrystalline diamond and ultracrystalline diamond.

* * * * *